United States Patent [19]
Henderson et al.

[11] Patent Number: 6,051,417
[45] Date of Patent: Apr. 18, 2000

[54] PROSTATE CANCER DRUG SCREENING USING HKLK2 ENHANCER

[75] Inventors: Daniel R. Henderson, Palo Alto; Eric R. Schuur, Cupertino; Henry G. Lamparski, San Mateo; De-Chao Yu, Foster City, all of Calif.

[73] Assignee: Calydon, Inc., Sunnyvale, Calif.

[21] Appl. No.: 08/906,192

[22] Filed: Aug. 4, 1997

Related U.S. Application Data

[63] Continuation-in-part of application No. 08/692,759, Aug. 6, 1996, Pat. No. 5,783,435.
[51] Int. Cl.[7] .............................. C12N 1/20; C12Q 1/68; C12Q 1/66; G01N 33/48
[52] U.S. Cl. .............................. 435/252.3; 435/6; 435/8; 436/63; 436/64
[58] Field of Search .................................. 435/6, 8, 252.3; 436/63, 64

[56] References Cited

FOREIGN PATENT DOCUMENTS

| | | |
|---|---|---|
| WO 95/06754 | 3/1995 | WIPO . |
| WO 95/19434 | 7/1995 | WIPO . |
| WO 96/14875 | 5/1996 | WIPO . |

OTHER PUBLICATIONS

Carson–Jurica et al., "Steroid receptor family: structure and functions" *Endocr. Rev.* (1990) 11(2):201–220.
Charlesworth et al., "Detection of a prostate–specific protein, human glandular kallikrein (hK2), in sera of patients with elevated prostate–specific antigen levels" *Urology* (1997) 49(3):487–493.
Culig et al., "Androgen receptor activation in prostatic tumor cell lines by insulin–like growth factor–I, keratinocyte growth factor, and epidermal growth factor" *Cancer Research* (1994) 54:5474–78.
*Current Protocols in Molecular Biology* (F.M. Ausubel et al., eds., 1987), Ch. 9, table of contents and title page enclosed herewith.
Dai et al., "Two androgen response elements in the androgen receptor coding region are required for cell–specific up–regulation of receptor messenger RNA" *Molecular Endocrinology* (1996) 10(12):1582–94.
Darson et al., "Human glandular kallikrein 2 (hK2) expression in prostatic intraepithelial neoplasia and adenocarcinoma: a novel prostate cancer marker" *Urology* (1997) 49(6):857–862.
de Wet et al., "Firefly luciferase gene: structure and expression in mammamlian cells" *Molecular and Cellular Biology* (1987) 7(2):725–737.
Decensi et al., "Effect of the nonsteroidal antiandrogen nilutamide on adrenal androgen secretion" *The Prostate* (1994) 24:17–23.
Lindzey et al., "Molecular mechanisms of androgen action" *Vitamins and Hormones* (1994) 49:383–432.
Morris, "hGK–1 a kallikrein gene expressed in human prostate" *Clin. Exp. Pharm. Physiol.* (1989) 16(4):345–351.

Murtha et al., "Androgen induction of a human prostate–specific kallikrein, hKLK2: characterization of an androgen response element in the 5' promoter region of the gene" *Biochem* (1993) 32:6459–6464.
Pang et al., "Prostate tissue specificity of the prostate–specific antigen promoter isolated from a patient with prostate cancer" *Hum. Gene Therapy* (1995) 6:1417–1426.
Qiu et al., "In situ hybridization of prostate–specific antigen mRNA in human prostate" *J. Urol.* (1990, 144(6):1550–56.
Schedlich et al., "Primary structure of a human glandular kallikrein gene" *DNA* (1987) 6(5):429–437.
Schuur et al., "Prostate–specific antigen expression is regulated by an upstream enhancer" *J. Biol. Chem.* (1996) 271(12):7043–7051.
Tilley et al., "Characterization and expression of a cDNA encoding the human androgen receptor" *Proc. Natl. Acad. Sci. USA* (1989) 86:327–331.
Tremblay et al., "Immunohistochemical study suggesting a complementary role of kallikreins hK2 and hK3 (prostate–specific antigen) in the functional analysis of human prostate tumors" *Am. J. Pathol.* (1997) 150(2):455–459.
Wolf et al., "Transcriptional regulation of prostate kallikrein–like genes by androgen" *Molec. Endocrinol.* (1992) 6(5):753–762.
Young et al., "Tissue–specific and hormonal regulation of human prostate–specific glandular kallikrein" *Biochem* (1992) 31(3):818–824.
Zhou et al., "The androgen receptor: an overview" *Recent Prog. Horm Res.* (1994) 49:249–274.
Williams et al., "Advantages of Firefly Luciferase as a Reporter Gene: Application to the Interleukin–2 Gene Promoter", *Analyt. Biochem.* (1989) 176(1):28–32.

*Primary Examiner*—Yvonne Eyler
*Attorney, Agent, or Firm*—Morrison & Foerster, LLP

[57] ABSTRACT

Screening of compounds for activity toward inhibition of prostate cancer cell proliferation is provided. A cell line containing an expression construct comprising a transcriptional initiation region of a prostate specific enhancer from a human glandular kallikrein (hKLK2) gene is employed which can be used in conventional equipment for determining activity of compounds, where the cell line uses a marker whose expression is responsive to therapeutically active compounds.

11 Claims, 6 Drawing Sheets

PROSTATE CANCER DRUG SCREENING USING HKLK2 ENHANCER

CROSS-REFERENCE TO RELATED APPLICATIONS

This application is a continuation-in-part of U.S. Ser. No. 08/692759, filed Aug. 6, 1996, now issued as U.S. Pat. No. 5,783,435.

TECHNICAL FIELD

The present invention relates to screening methods for identifying compounds useful in the treatment of prostate cancer.

BACKGROUND

Prostate cancer is the fastest growing neoplasm in men with an estimated 244,000 new cases in the United States being diagnosed in 1995, of which approximately 44,000 deaths will result. Hormonal ablation therapy, either surgically or chemically with anti-androgens, is the main stay of treatment for advanced carcinoma of the prostate. However, androgen ablation therapy failed within 12–18 months with the disease becoming androgen independent. Following the failure of androgen therapy, the median patient survival time is eight months. Other approaches to treating prostate cancer—external radiation, radioactive seed therapy, cryotherapy, etc.—are directed toward organ confined disease of the prostate and are unable to treat metastatic tumors.

The prostate-specific antigen (PSA), a member of the human kallikrein gene family, is a Mr=34,000 chymotrypsin like protein that is synthesized exclusively by normal, hyperplastic, and malignant prostatic epithelia. Hence, the PSA's tissue-specific relationship has made it an excellent biomarker for identifying benign prostatic hyperplasia (BPH) and prostatic carcinoma (CaP), hereinafter CaP. Normal serum levels of PSA in blood are typically below 5 ng/ml, with elevated levels indicative of BPH or CaP. Serum levels of 200 ng/ml have been measured in end-stage metastatic CaP.

Another member of the kallikrein gene family, human glandular kallikrein-1 (hGK-1 or hKLK2, encoding the hK2 protein), shares a number of characteristics with PSA. First, both are expressed exclusively in the prostate and are up-regulated by androgens primarily by transcriptional activation. Wolf et al. (1992) *Molec. Endocrinol.* 6:753–762. Morris (1989) *Clin. Exp. Pharm. Physiol.* 16:345–351; Qui et al. (1990) *J Urol.* 144:1550–1556; Young etal. (1992) *Biochem.* 31:818–824. Second, hKLK2 and PSA mRNAs are synthesized and co-localize only in prostatic epithelia. Third, hKLK2 and PSA exhibit a high degree of amino acid sequence identity. Schedlich et al. (1987) DNA 6:429–437. Fourth, they have similar regulatory elements. There is approximately 80% nucleotide sequence identity between PSA and hKLK2 in the 5'-flanking region from −300 to -1 relative to the transcription initiation site. Young et al. (1992) *Biochem.* 31:818–824. Each promoter contains an androgen responsive element (ARE); their respective ARE's differ from one another by only 1 nucleotide. Schedlich et al. (1987) *DNA* 6:429–437; Murtha et al. (1993) *Biochem.* 32:6459–6464.

The levels of hK2 found in various tumors and in the serum of patients with prostate cancer differ substantially from those of PSA. Circulating hK2 in different relative proportions to PSA has been detected in the serum of patients with prostate cancer. Charlesworth et al. (1997) *Urology* 49:487–493. Expression of hK2 has been detected in each of 257 radical prostatectomy specimens analyzed. Darson et al. (1997) *Urology* 49:857–862. The intensity and extent of hK2 expression, detected using specific antibodies, increased from benign epithelium to high-grade prostatic intraepithelial neoplasia (PIN) and adenocarcinoma, whereas PSA and prostate acid phosphatase (PAP) displayed an inverse pattern of immunoreactivity. Darson et al. (1997) *Urology* 49:857–862. Indeed, it has been reported that a certain percentage of PSA-negative tumors have detectable hK2. Tremblay et al. (1997) *Am. J Pathol.* 150:455–459.

As mentioned above, both PSA and hKLK2 genes are up-regulated by androgens primarily by transcriptional activation. Androgen induction of gene expression requires the presence of an androgen receptor (AR). Typically, an androgen diffuses passively into the cell where it binds AR. The androgen-activated AR binds to specific DNA sequences called androgen-responsive elements (AREs or ARE sites). Once anchored to an ARE, the AR is able to regulate transcriptional activity in either a positive or negative fashion. Lindzey et al. (1994) *Vitamins and Hormones* 49: 383–432.

The AR belongs to a nuclear receptor superfamily whose members are believed to function primarily as transcription factors that regulate gene activity through binding to specific DNA sequences, hormone-responsive elements. CarsonJurica et al. (1990) *Endocr. Rev.* 11: 201–220. This family includes the other steroid hormone receptors as well as the thyroid hormone, the retinoic acid and the vitamin $D_3$ receptors. The progesterone and glucocorticoid receptor are structurally most closely related to the AR. Tilley et al. (1989) *Proc. Natl. Acad Sci. USA* 86: 327331; Zhou et al. (1994) *Recent Prog. Horm. Res.* 49: 249–274; and Lindzey et al. (1994) *Vit. Horm.* 49: 383–432.

The AR gene itself is a target of androgenic regulation. In the prostate cancer cells lines PC3 and DU145, which do not express an endogenous AR, androgenic up-regulation of AR cDNA expression occurred in the transfected cells. Dai et al. (1996). Androgenic up-regulation of AR mRNA and protein was observed in PC3 cells that were stably transfected with the AR CDNA, suggesting that AR mRNA regulation also occurs when the CDNA is organized into chromatin. Dai et al. (1996).

The characterization of genes whose expression is limited to the prostate allows the development of screening methods which can identify substances capable of specifically altering the expression of prostate-specific genes.

In the last few years, numerous techniques have been developed for producing vast arrays of potential drug-like compounds. These compounds include not only oligomers, such as oligopeptides and oligonucleotides, but also synthetic organic compounds based on various core structures. In addition, various natural sources have been screened for active compounds, such as those found in jungles, the ocean and the like. Thus, there is a great proliferation of available compounds for screening for physiological activity.

The process of identifying prospective compounds having therapeutic activity is primarily held back by the absence of useful screening assays. In order for a screening assay to be useful, it should be capable of automation, allow for the screening of large numbers of samples without requiring extensive equipment or housing, be relatively inexpensive, and provide for a clear indication of activity. There is, therefore, substantial interest in identifying new screening assays which would allow for the screening of compounds which may have therapeutic activity in relation to prostate cancer.

SUMMARY OF THE INVENTION

Methods and compositions are provided for screening therapeutic agents for the treatment of prostate cancer. The methods employ a PSA expressing stably transformed epithelial cell line comprising a construct of the PSA gene enhancer/promoter and a marker gene, e.g. luciferase. The cells are shown to be responsive to the addition of androgen agonists and antagonists by the modified expression of the marker gene. The methods also employ a cell line derived from the prostate, which cell line is stably transformed with a construct comprising a transcriptional control region of a gene, such as PSA or hKLK2, whose expression is substantially limited to cells of the prostate, and a reporter gene. Alterations in the levels of reporter gene product in the presence of a candidate agent or compound are indicative of a potential therapeutic agent.

Accordingly, in one aspect, the invention includes a method for screening drugs for the treatment of prostate cancer employing PSA expressing cells comprising an expression construct which comprises a transcriptional initiation region of the prostate specific antigen enhancer and a promoter and a gene whose expression product provides a detectable signal, wherein said gene is under the transcriptional control of said transcriptional initiation region, said method comprising combining said PSA expressing cells with a candidate drug in the presence of an androgen for sufficient time for detectable expression of said gene, and detecting the level of expression of said gene as compared to the level of expression in the absence of said candidate drug.

In another aspect, the invention provides a method A method for screening drugs for the treatment of prostate cancer employing PSA expressing cells comprising an expression construct which comprises a transcriptional initiation region of the prostate specific antigen enhancer and a promoter and a gene encoding an enzyme which catalyzes a reaction resulting, in a detectable signal, wherein said gene is under the transcriptional control of said transcriptional initiation region, said method comprising combining said PSA expressing cells with a candidate drug in the presence of methyl trienolone or dihydrotestosterone for sufficient time for detectable expression of said enzyme, lysing said PSA expressing cells to provide a lysate and adding the substrate of said enzyme to said lysate, and detecting the level of expression of said enzyme as compared to the level of expression in the absence of said candidate drug.

In another aspect, the invention provides a method for screening compounds for the treatment of prostate cancer employing mammalian cells comprising an expression construct, said expression construct comprising an enhancer of a prostate-specific gene and a promoter and a reporter gene whose expression product provides a detectable signal, wherein said reporter gene is under the transcriptional control of said enhancer, said method comprising the steps of combining said cells with a candidate compound for a sufficient time for detectable expression of said reporter gene, and detecting the level of expression of said reporter gene as compared to the level of expression in the absence of said candidate compound.

BRIEF DESCRIPTION OF THE DRAWINGS

FIG. 3A shows induction, expressed in relative light units (RLU) per µg total protein, of luciferase expression by the hKLK2 promoter-containing construct CN299 (stippled bars) or by the hKLK2 promoter/enhancer-containing construct CN322 (solid bars) in the presence of 0 nM or 0.5 nM R1881. FIG. 3B shows the fold induction calculated by comparing CN322 RLU/µg protein with CN299 RLU/µg protein in the presence of 0.5 nM R1881.

FIG. 4A shows luciferase activity, expressed as RLU/µg protein, from cultures incubated in the presence of 0, 0.01, 0.1, 1, or 10 nM R1881. FIG. 4B shows fold induction calculated by comparing RLU/µg protein at a given concentration to RLU/µg protein at 0 nM R1881.

DESCRIPTION OF THE SPECIFIC EMBODIMENTS

Figure 1A:
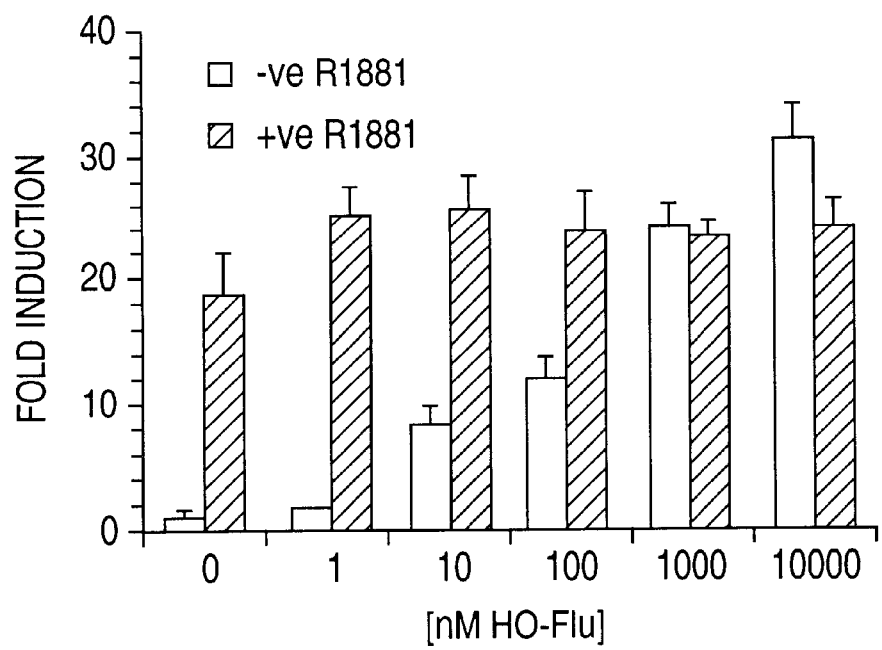
FIGS. 1A and 1B is a bar graph of anti-androgen induction/inhibition on luciferase expression by the cell line CN1013, FIG. 1A indicating induction by hydroxyflutamide, and FIG. 1B by cyproterone acetate, before (white bars) and after (dark bars) induction with 1 nM R1881.

Methods are provided for screening compounds for therapeutic effect against prostate cancer. The methods comprise adding the compound in an appropriate medium to PSA producing cells into which has been stably introduced a genetic construct comprising the enhancer/promoter of the prostate-specific antigen (PSA) with a structural gene under the transcriptional regulation of the PSA enhancer/promoter.

Alternatively, the methods comprise adding the compound in an appropriate medium to cells, preferably derived from the prostate, into which has been stably introduced a genetic construct comprising a transcriptional control region of a prostate-specific gene with a structural gene under the transcriptional regulation of the prostate-specific gene transcriptional control region, which structural gene provides for a detectable, quantifiable signal. Examples of prostate-specific genes include, but are not limited to, PSA and hKLK2. By measuring the effect of the candidate compound on the level of signal observed as compared to a basal level, one can evaluate the potential of the compound as a therapeutic agent for the treatment of prostate cancer. Particularly, anti-androgenic activity can be evaluated as indicative of therapeutic effects for prostate cancer, although any compound which modifies the expression of a prostate-specific gene, whatever its mode of action, may be considered a candidate compound.

Cells which are suitable for use in the screening methods of the present invention are mammalian cells in which at least one prostate-specific gene is expressed in the cells. Preferably, the cells are prostate cells, more preferably expressing endogenous androgen receptor, even more preferably prostate epithelial cells expressing endogenous androgen receptor. Preferably, the cells employed display expression of the prostate-specific gene whose transcriptional control region, in whole or in part, is contained within the construct used to stably transform the cells. Alternatively, the cells need not be derived from the prostate as long as the normal function of the transcription regulatory elements of the prostate-specific gene is maintained. This may be achieved, for example, by co-transfecting the cell with a gene encoding a product necessary for the normal function of the promoter/enhancer region of the prostate-specific gene. For example, if the promoter/enhancer region of the prostate-specific gene is inducible by androgen, it may be necessary to co-transfect into the cells a construct which encodes and allows expression of a gene encoding an androgen receptor.

"Androgen receptor" as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones. Encompassed in the term "androgen receptor" are mutant forms of an androgen receptor, as long as the function is sufficiently preserved. Mutants include androgen receptors with amino acid additions, insertions, truncations and deletions, as long as the function is sufficiently preserved.

The term "prostate-specific gene" as used herein indicates a gene whose expression is substantially limited to cells of the prostate, in particular to prostate epithelial cells, and whose expression is substantially undetectable in normal cells derived from tissues other than the prostate.

The term "transcriptional control region" as used herein encompasses enhancers, promoter elements and/or any other nucleotide sequence which controls the level of transcription of a coding region.

The prostate-specific gene whose transcription control region is operably linked with a reporter gene may or may not be one whose expression in prostate cells or cell derived from the prostate is inducible, but preferably is inducible. The term "inducible gene" is used herein to indicate a gene which is normally transcriptionally silent in prostate cells or whose expression is substantially undetectable, and whose expression, in the presence of an appropriate inducing agent, is increased at least 10fold, more preferably at least about 10- to about 50- fold, even more preferably about 50- to about 200-fold, relative to expression in the absence of the inducing agent.

An inducing agent can be any compound which is added to the growth environment of the cell and which, upon contact with and/or entry into the cell, results in the expression of a specific gene or set of genes. For the purposes of the present invention, an "appropriate inducing agent" is one which specifically induces the expression of a gene which is operably linked to a reporter gene. For example, both PSA and hKLK2 enhancers are inducible with androgen. An example of an inducing agent used is R1881, a testosterone analog.

In one embodiment, the cells which are employed in the screening are stable prostate cancer cell lines which express PSA, particularly based on the LNCaP cell line, which are cells derived from a metastatic tumor isolated from a lymph node. This cell line has been established for an extended period of time, stably maintains expression of PSA, and is readily grown in conventional media.

In this embodiment, the subject cells are produced by introducing an expression construct into a stable prostate cancer cell line expressing PSA at least a level of 10 to 20 ng/mL per $10^6$ cells per day. The expression construct comprises as the transcriptional initiation regulatory region, the PSA enhancer with the PSA promoter or a different promoter region, usually the PSA promoter. The 5' non-coding region of the PSA gene may include the region from 0 (the site of transcription initiation) to −6000 or may be truncated, to provide only those sequences essential for the enhancer region and the promoter region. Thus, the particular regions include the enhancer active sequences between −5824 and −3738 with the promoter active region, for the PSA gene, the region from about −560 to +7.

In another embodiment, the cells employed are mammalian cells (preferably prostate cells, even more preferably LNCaP cells) and the expression construct comprises, as the transcriptional initiation regulatory region, an hK2 enhancer with a promoter which may be an hKLK2 promoter or a heterologous promoter. The 5' non-coding region of the hKLK2 gene may include the region from +33 (relative to the site of transcription initiation) to −12,014 or may be truncated to provide only those sequences essential for enhancer function and/or promoter function. Particular regions include an approximately 1.7 kb enhancer active fragment from −5155 to 3387 relative to the transcription start site (nucleotides 6859 to 8627 of SEQ ID NO: 1), with the promoter active region being the region from about −600 to about +33 relative to the transcription start site (from about 11420 to 12047 of SEQ ID NO:1).

The DNA sequence as such can vary in length and/or nucleotide sequence as long as the requisite function is maintained.

This transcription initiation regulatory region may then be joined to a marker gene which provides for a detectable, desirably quantifiable, signal. Of particular interest are genes which provide for luminescence, such as luciferase, aequorian, β-galactosidase, chloramphenicol acetyl transferase, etc. In addition, one may provide for a marker for selection comprising a constitutive transcriptional initiation region and an antibiotic resistance gene, e.g. neo. In this way, one may select for those cells which have the expression construct stably integrated.

Marker genes, or reporter genes, which may be employed are known to those skilled in the art and include, but are not limited to, luciferase; aequorian (i.e., green fluorescent protein from *Aequorea Victoria*); β-galactosidase;, chloramphenicol acetyl transferase; immunologically detectable protein "tags" such as human growth hormone; and the like. See, for example, Current Protocols in Molecular Biology (F. M. Ausubel et al., eds., 1987) and periodic updates. Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays. Many of these assays are commercially available.

The construct may be prepared in accordance with conventional ways, introducing each of the components of the construct into a plasmid by employing convenient restriction sites, PCR (polymerase chain reaction) to introduce specific sequences at the terrnini, which may include providing for restriction sites, and the like. After the expression construct has been prepared, it may be introduced into the cells by any convenient means.

Methods for introducing the expression construct into the cells or cell lines include transfection, complexing with cationic compounds, lipofection, electroporation, and the like. The cells may be expanded and then screened for the presence of the expression construct. Where an antibiotic resistance gene has been introduced, the cells may be selected for antibiotic resistance and the antibiotic resistance cells then screened for luminescence under appropriate conditions. In the absence of the antibiotic resistance, the cells may be directly screened for luminescence. Conveniently, the assay for luminescence is performed on a lysate using conventional reagents.

After selecting clones which demonstrate high levels of luciferase activity when activated, the induction ratio may be further enhanced by performing limiting dilution with the cells and screening the resulting clones. In this manner, the induction may be at least 20 fold when induced with an inducing agent such as 0.1–1.0 nM R1881, preferably at least about 50 fold, and more preferably at least about 100 fold. Usually, the induction will not exceed about 500 fold.

When the prostate-specific gene used to transform the cell is hormone-inducible, cells are desirably grown in hormone-free medium, e.g. RPMI medium supplemented with 10% fetal bovine serum, 100 units/ml penicillin and 100 μg/ml streptomycin, and assayed in hormone spiked medium, e.g. 10% strip-serum RPMI with hormone. Desirably, the cells should not have been passaged more than about 50 times, more desirably not more than about 25 times.

The luminescence may be determined in accordance with conventional commercial kits, e.g. enhanced luciferase assay kit (Analytical Luminescence Laboratory, MI). The cells may be distributed in multiwell plates which can be accommodated by a luminometer. A known number of cells is introduced into each one of the wells in an appropriate medium, the candidate compound added, and the culture maintained for at least 12 hours, more usually at least about 24, and not more than about 60 hours, particularly about 48 hours. The culture is then lysed in an appropriate buffer, using a non-ionic detergent, e.g. 1% triton X-100. The cells are then promptly assayed. In conjunction with the candidate compound, an inducing compound, e.g. androgens, will also be added such as methyl trienolene (R1881), or dihydrotestosterone (DHT). The concentration of these inducing agents will vary depending upon the nature of the agent, but will be sufficient to induce expression. The concentration with R1881 will generally be in the range of about 0.1–10 nM, preferably about 1 nM.

Any other technique for detecting the level of luminescence may be used. The particular manner of measuring luminescence is not critical to the invention.

The following examples are offered by way of illustration and not by way of limitation.

EXAMPLES

Example 1

Preparation and Testing of PSA-Luciferase Constructs
Materials and Methods

Cells and Culture Methods. LNCaP cells were obtained at passage 9 from the American Type Culture Collection (Rockville, Md.). LNCaP cells were maintained in RPMI 1640 medium (RPMI) supplemented with 10% fetal bovine serum (FBS; Intergen Corp.), 100 units/mL of penicillin, and 100 units/mL streptomycin. LNCaP cells being assayed for luciferase expression were maintained in 10% strip-serum (charcoal/dextran treated fetal bovine serum to remove T3, T4, and steroids; Gemini Bioproduct, Inc., Calabasas, Calif.) RPMI. The cells were periodically tested for the production of PSA which was consistently above 20 ng/ml per day.

Selection for a stably integrated plasmid DNA was performed in RPMI medium containing G418 (GibcoBRL, N.Y.). The level of G418 in RPMI was decreased from 500 to 100 μg/mL after selection of the parental LNCaP clones for evaluation; these clones were maintained in 100 μg/mL G418 at all times prior assaying. Subclones having enhanced luciferase activity were obtained from the parental cell line by the method of limited dilution cloning.

PSE-Luciferase (CNI) Plasmid Constructs. The luciferase gene from *Photinus pyralis* from the plasmid pJD206 (de Wet et al. *Molecular and Cellular Biology* (1987) 7:725–737) was excised by cleavage with restriction enzymes HindIII and BamHI, then ligated into similarly cleaved pUC 18. This plasmid was then cleaved with HindIII and Kpnl again to remove the luciferase fragment which was then ligated into similarly cleaved pBluescript KSII(+) (Stratagene). The resulting plasmid was designated LB78. The 5.8 kb HindIII fragment containing the PSA gene upstream region was excised from the plasmid CN0 (Schuur et al., *J Biol. Chem.* (1996) 271:7043–7051) and ligated to HindIII-cleaved LB78. A clone was selected with the cap site of the PSA gene in the PSA gene fragment adjacent to the beginning of the luciferase gene to drive its synthesis. The resulting clone was designated CN1 (PSE-Luc).

Transfections of LNCaP Cells. For transfections, LNCaP cells were plated out at a cell density of $5 \times 10^5$ cells per 6-cm culture dish (Falcon, N.J.) in complete RPMI. DNAs were introduced into LNCaP cells after being complexed with a 1/1 molar lipid mixture of N-[1-(2,3-dioleyloxy)propyl-N, N,N-trimetylammonium chloride (DOTAP; Avanti Polar Lipids, AL) and dioleoyl-phosphatidylethanolamine (DOPE; Avanti Polar Lipids, AL); DNA/lipid complexes were prepared in serum-free RPMI at a 2/1 molar ratio. Typically, 8 μg (24.2 nmole) of DNA was diluted into 200 μL of incomplete RPMI and added dropwise to 50 nmole of transfecting, lipids in 200 μL of RPMI with gentle vortexing to insure homogenous mixing of components. The DNA/lipid complexes were allowed to anneal at room temperature for 15 minutes prior to their addition to LNCaP cells. Medium was removed from LNCaP cells and replaced with 1 mL of serum-free RPMI followed by the dropwise addition of DNA/lipid complexes. Cells were incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 μL media and assayed. Varying amounts of drugs (e.g. androgens and anti-androgens) were added 16 hours later and assayed for luciferase activity 32 hours thereafter.

Generation of a stably transfected cell line expressing luciferase was accomplished by co-transfecting the plasmid pcDNA3 with PSE-Luc. The neomycin gene of pcDNA3 confers resistance to the antibiotic G418, allowing selection of stably transfected LNCaP cells. LNCaP cells were co-transfected with PSE-Luc and pcDNA3 as described for transient transfections. Briefly, 1 μg of pcDNA3 and 1–10 μg of PSE-Luc were diluted into 200 μL of RPMI and complexed with two molar equivalents of DOTAP/DOPE (1:1) in 200 μL RPMI. Addition of DNA to lipids was dropwise with gentle vortexing to homogeneously mix the samples. After annealing the complexes for 15 minutes, they were added dropwise to LNCaP cells in I mL RPMI and incubated overnight (12 hours) at 37° C. Media/DNA-lipid complexes were removed from the tissue culture plates and supplemented with complete RPMI containing 500 μg/mL G418. The selection media was kept at 500/μ/mL G418 for three weeks before being lowered to 250 μg/mL. G418 resistant colonies appeared after four weeks and were allowed to grow until visible by eye, upon which colonies were trypsinized (0.25% trypsin) and transferred to a 24 well tissue culture plate, followed by further expansion. Clones were assayed for luciferase expression after they had reached 3–5×10$^6$ cells. Screening identified the clone CN1013 which was selected for further study. A clone 5–10 fold more active than CN 1013, designated CN 101 3.7, was obtained by subcloning the parental line once by limiting dilution.

Induction and Assaying of Transient and Stable PSE-Luc/LNCaP Cells. For both transient and stably transfected LNCaP cells, a variety of androgens and anti-androgens— methyl trienolone (R1881, DuPont NEN), dihydrotestosterone (DHT, Sigma), cyproterone acetate (CA and hydroxyflutamide (Ho-Flu)—were used to induce expression of the luciferase reporter gene. Androgens or anti-androgens were prepared at 3×concentrations in 10% strip-serum RPMI and added as 50 μL aliquots to each well of the 96-well plate. Cells were incubated with either androgens or anti-androgens for 48 hours before assaying. Assays were done in triplicate or quadruplicate. The concentration of dihydrotestosterone (DHT) was measured by the Testosterone ELISA Kit (Neogen Corporation). The assay has 100% cross reactivity with DHT.

In the case of stably transfected PSE-Luc/LNCaP clones, media was removed and cells washed with PBS (2×20 mL). The clonal cells were then maintained in 10% strip-serum RPMI (phenol red free) for 24 hours prior to trypsinizing and replating into an opaque 96-well plate—40,000 cells/well per 100 μL media. Cells were allowed to become adherent overnight before the addition of either androgens or anti-androgens. Incubation of clonal cells in strip-serum RPMI prior to induction with drug(s) substantially lowered background luciferase expression.

The luciferase assay of both transient and stably transfected cells was performed in the same manner. After induction of cells with androgens or anti-androgens for 48 hours, media was removed and 50 μL of lysis reagent added (0.1 M potassium phosphate buffer at pH 7.8, 1% Triton X-100, 1 mM dithiothreitol, 2 mM EDTA) to each well. Cells were assayed within 15 minutes of lysis or stored at −80° C. until analysis. Storage of cell lysates at −80° C. for five days or less did not result in significant loss of luciferase activity.

The Enhanced Luciferase Assay Kit (Analytical Luminescence Laboratory, MI) was used to quantitate the extent of luciferase activity from PSE-Luc transfected LNCaP cells. A Dynatech 3000 96-well plate luminometer (Dynatech, VA) was used to measure the amount of light generated from the assay. The instrument was run in the Enhanced Flash Mode, employing a dual injector system for substrate addition. Optimal assay conditions and Luminometer parameters were as follows: addition of 60 μL of Substrate A (buffer), 1 second delay, addition of 60 μL of Substrate B (luciferin reagent), 1 second delay, integrate signal for 3 seconds. The results are depicted as the integral sum in relative light units (RLUs). The extent of induction by androgens/anti-androgens, e.g. fold induction, was determined by: fold induction=RLUs [x nM drug]/RLUs [0 nM drug].

CMV-Luc/LNCaP Cell Line. Transfections of the control plasmid, CMV-Luc, into LNCaP cells were done in the same fashion as for PSE-Luc. The stable cell line CN1006, containing CMV-Luc, was obtained by selection with G418. The luciferase assay was performed as described above.

Results

Transient Transfections of LNCaP Cells with PSE-Luc. The effectiveness of utilizing PSE-Luc in transient transfections as a transcription screening assay for agonist/antagonist type molecules was examined in LNCaP cells. This transcription assay was evaluated for its use in a 96-well format. The androgens, methyl trienolone (R1881) and dihydrotestosterone (DHT), were used to induce different degrees of luciferase expression under the control of the prostate-specific enhancer.

The inducibility of PSE-Luc by the synthetic androgen R1881 in transiently transfected LNCaP cells was determined. Cells were plated into an opaque 96-well plate at a cell density of 4×10$^4$ cells/well per 100 μL, followed by 50 μL of a 3×media solution containing either R1881 or DHT. Cells were incubated for 48 hours, lysed and assayed for luciferase expression. The extent of induction was determined by dividing the amount of luciferase expression (RLUs) at X nM hormone by the amount of expression without hormone. At 0 nM R1881, luciferase expression in transfected LNCaP cells was similar to background levels (approximately 1–5 RLUs). The addition of 1–50 nM R1881 resulted in an approximately 275 fold induction of luciferase expression (3,000–3,500 RLUs) over uninduced transfected cells. Peak levels of luciferase expression were obtained at 1 nM R1881, which closely corresponds to physiological levels of androgen. Variations in the amount of DNA/Lipid complexes used in transient transfections resulted in comparable results, however lower DNA concentrations (e.g. 1 and 2 μg DNA) gave smaller RLU values after induction. Lastly, %CV varied ranging from 10–30%.

A second androgen, dihydrotestosterone (DHT), was evaluated for its inducibility of transiently transfected LNCaP cells. DHT is a naturally occurring human androgen and the reductive analog of testosterone. The extent of fold induction increased with increasing concentration of DHT. Peak levels of approximately 100 fold were obtained over the background value of 25 RLUs for DHT concentrations of 100 and 200 nM (e.g. 2,500–3,000 RLUs). A comparison of R1881 and DHT shows that approximately 100 fold more DHT is required relative to R1881 to obtain comparable luciferase activity. The difference in fold induction between the two androgens, e.g. 100 vs. 250 fold induction, can be explained by a 2 fold higher background signal for the DHT (12 vs. 25 RLUs), which likely resulted from the particular experimental procedures employed. However, the overall peak expression levels stimulated by the two androgens are comparable. The higher concentration of DHT required to achieve the same luciferase expression levels obtained with R1881 is addressed later.

Androgen and Anti-androgen Responsiveness of Stably Transfected PSE-Luc/LNCaP Cell Line. LNCaP cells were co-transfected with PSE-Luc and pcDNA3 containing the neomycin gene. LNCaP clones containing both genes were selected with G418 and examined for luciferase expression after induction with either androgen or anti-androgens. As in the case of transient transfections with PSE-Luc, the assay is evaluated in the 96-well format for high throughput screening (HTS) of potential agonist/antagonist.

The hormones R1881 and DHT were utilized to screen for androgen-responsive LNCaP clones containing the PSE-Luc genes. Two clones, designated CN1010 and CN1013, exhibited luciferase activity upon incubation in lnM R1881 and were characterized further with varying concentrations of R1881 and DHT. The androgen-responsiveness profile of CN 1013 is similar to that obtained for transient transfections. Peak values of R1881 induction were obtained at physiological levels (0.1–1 nM), while DHT required 100–200 fold greater amounts for comparable expression. The $EC_{50}$ of R1881 in CN1013 was 0.075nM.

Figure 1B:
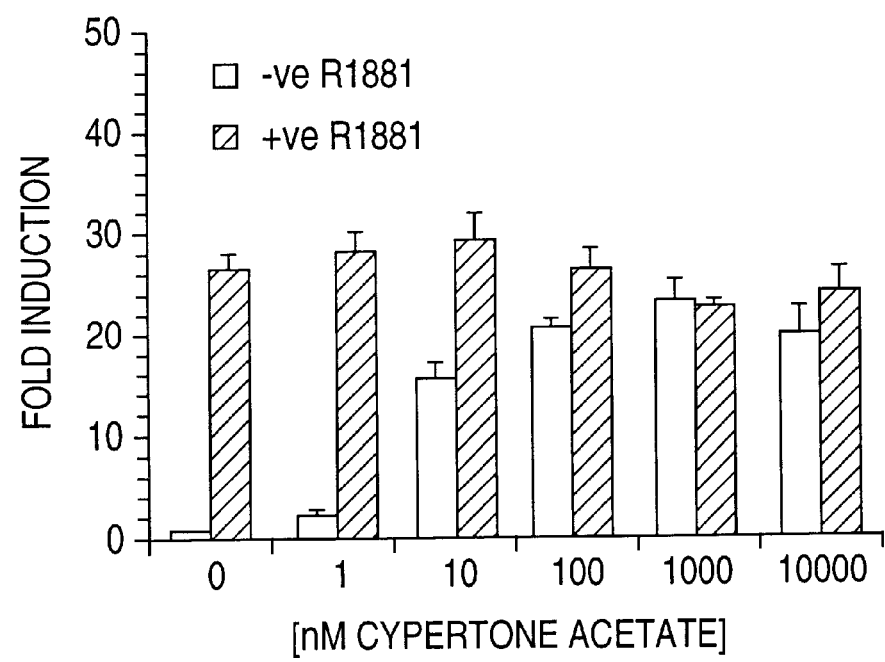

The luciferase responsiveness of CN 1013 to anti-androgens, hydroxyflutamide (HO-Flu) and cyproterone acetate (Cypro. A), as well as their antagonist behavior to R1881 (1 nM) induced cells was evaluated. Incubation of CN 1013 with either anti-androgen resulted in luciferase expression levels similar to that obtained for R1881, but only at elevated concentrations of 100–1,000 fold higher (FIGS. 1A and 1B): zero or minimal expression was observed at physiological concentrations. The anti-androgens ability to inhibit luciferase expression after induction with 1 nM R1881 is also shown in FIG. 1. At all anti-androgen concentrations examined, there was neither inhibition nor induction of luciferase expression after R1881 had been added. The addition of other non-steroidal intra-cellular receptor ligands unrelated to the androgen receptor, i.e. retinoic acid (RA), did not result in either induction or inhibition of CN1013.

The intra-assay %CVs of the stable cell line CN1013 typically varied between 5–10%. While the initial characterization of CN1013 resulted in %CV slightly higher than 10%, later experiments were able to lower the intra-assay %CV to an acceptable range (FIGS. 1A and 1B). Transient transfection assays yielded %CVs of 10–30%, whereas stable cell line assays (CN1013), yielded %CVs of 5–10%.

Metabolism of Dihydrotestosterone (DHT) in CN1013 Cell Line. The higher levels of DHT needed to induce luciferase expression in either CN1013 or transient transfections was investigated. The decrease of DHT concentration in CN1013 cells was measured kinetically utilizing the Testosterone ELISA Kit by Neogen Corporation (100% cross reactivity with DHT). The metabolism of DHT occurs rapidly within 1–4 hours of addition to CN1013 cells, while the DHT concentration remained constant when unexposed to CN1013 cells. The half life of 10 nM DHT in CN1013 cells was calculated to be approximately 1.1 hours. The metabolized product was not identified.

While the overall luciferase expression levels between transient transfections and CN1013 are similar (3000–4000 RLUs), the extent of fold induction upon androgen addition is approximately 5–10 times lower in the latter case due to significant background signal (e.g. 100–200 RLUs). The larger background signal is a result of the requirement of growing CN1013 in hormone containing RPMI. Incubation of CN1013 in 10% strip-serum RPMI (minus hormone) prior to plating into 96-well plates lowered background signal moderately. Further decreases in overall luciferase expression were observed with passage number of the cell line. A comparison of the RLUs at passage 5 and 15 showed an approximate 3–5 fold decrease in luciferase expression, however the overall level of induction remained identical.

The decrease in luciferase expression of CN1013 with increasing passage number resulted in the need to select subclones having enhanced expression levels. Subclones of PSE-Lue/LNCaP were obtained from the parental cell line CN1013 by limiting dilution. Screening of these clones produced a single active clone, designated CN1013.7, which was 5–10 times more active than the parental cell line yielding 100–200 fold induction with R1881.

Luciferase Expression of CMV-Luc/LNCaP Stable Cell Line. LNCaP clones containing the CMV-Luc gene were screened for stable expression of the luciferase gene (i.e. selection of stable cell line). A 3–4 fold increase in expression levels over the uninduced cells was observed upon the addition of 10–1000 nM androgen. A similar androgen stimulation of CMV-Luc expression in transient transfection of LNCaP cells was reported by Pang et al., Hum. Gene Ther. (1995) 6:1417–1426. The slight increase in expression levels was attributed to cell proliferation resulting from increased R1881 addition.

Example 2

Figure 2:
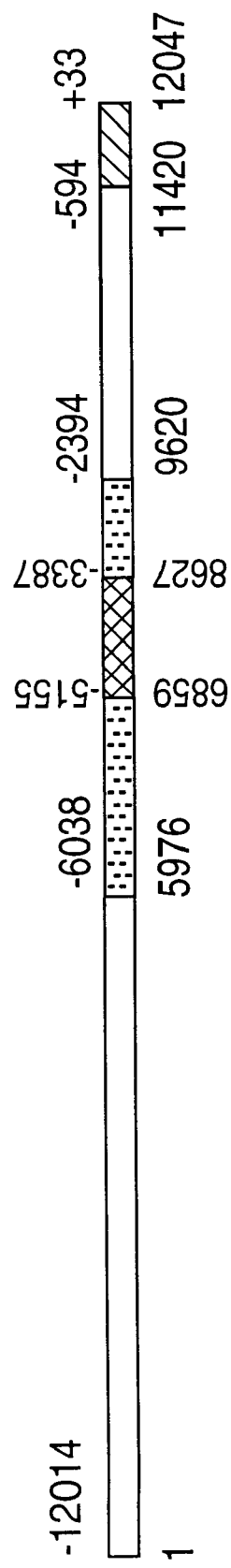
FIG. 2 is a schematic representation of the hK2 promoter/enhancer region (SEQ ID NO:1). The hatched bar represents the promoter region (Schedlich et al. (1987); GenBank accession number M18156); the dotted portion (including the solid portion) represents an enhancer region; the solid portion represents a smaller region with enhancer activity; and the transcription initiation site is indicated by a bent arrow.

Construction of Reporter Constructs in which Expression of Reporter Genes is Under the Control of the hKLK2 5'-flanking Region To assess the function of the DNA segment containing the enhancer, a series of constructs was generated by inserting the hKLK2 5'-flanking region, shown schematically in FIG. 2, upstream of the luciferase reporter gene. The activity of these fragments was compared with that of CN299, a plasmid with the full hKLK2 promoter (−605 to +33) driving the expression of firefly luciferase. The constructs are as follows:

To clone the hKLK2 full promoter an approximately 600 bp fragment was amplified with the oligonucleotides 41.100.1 and 42.100.2 (5'-GAT CAC CGG TGC TCA CGC CTG TAA TCT CAT CAC-3' (SEQ ID NO:2), 3PinAI site underlined). 42.100.2 corresponds to the upstream region of the hKLK2 promoter. The PCR product was then cloned into pGEM-T vector (Promega) to generate CN294.

CN299 is a plasmid containing the luciferase coding segment driven by the full hKLK2 promoter. The full promoter region was released from CN294 by NcoI-SacI digestion and ligated into a similarly cut pGL3-Basic (Promega) to generate CN299.

CN322 is a plasmid containing the entire structural gene of firefly luciferase driven by the human hKLK2 promoter and the other all regulatory elements. The entire 12 kbps hKLK2 5'-flanking region was excised from CN312 by SacII/SpeI digestion and ligated into SacII/SpeI digested pGL3-Basic to produce CN322.

CN324 is a luciferase construct containing the hKLK2 minimal promoter driving the luciferase coding region. The minimal hKLK2 promoter was released from CN317 by NcoI-SacI digestion and ligated into a similarly cut pGL3-Basic to generate CN324.

CN325 is the same as CN324, except that a XhoI site (instead of a PinAI site) was created at the 5'end of the minimal promoter.

CN355 was created by digesting CN340 with XhoI and KpnI. The released fragment (~-3.8 kbps) was ligated into CN325, upstream of the minimal promoter.

Example 3
Effects of the hKLK2 5'-flanking Region

Figure 3A:
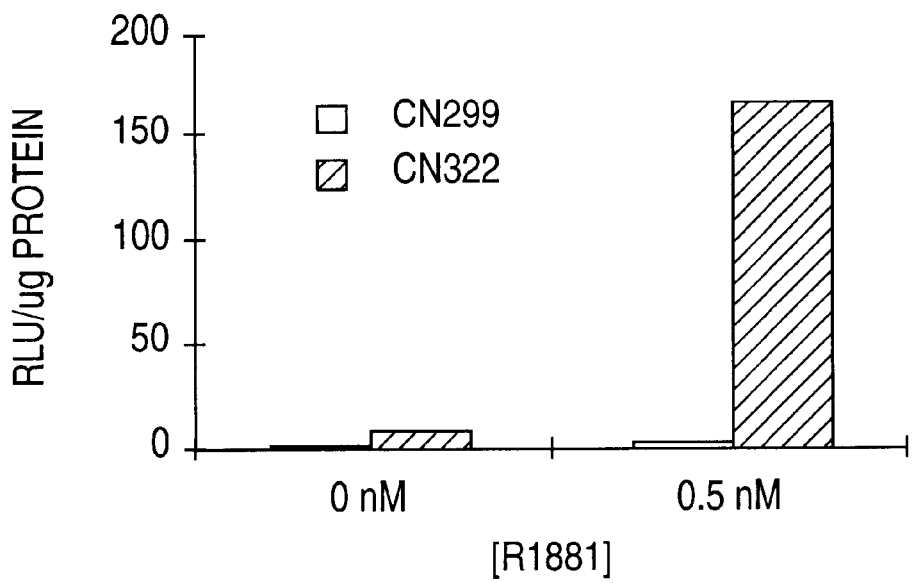
FIGS. 3A and 3B are bar graphs of testosterone analog R1881 induction of hKLK2 promoter/enhancer-driven luciferase expression in LNCaP (human metastatic prostate adenocarcinoma) cells. LNCaP cells were transfected with reporter gene constructs, incubated in the presence or absence of inducer, and, 48 hours after transfection, luciferase activity was measured.
Figure 3B:
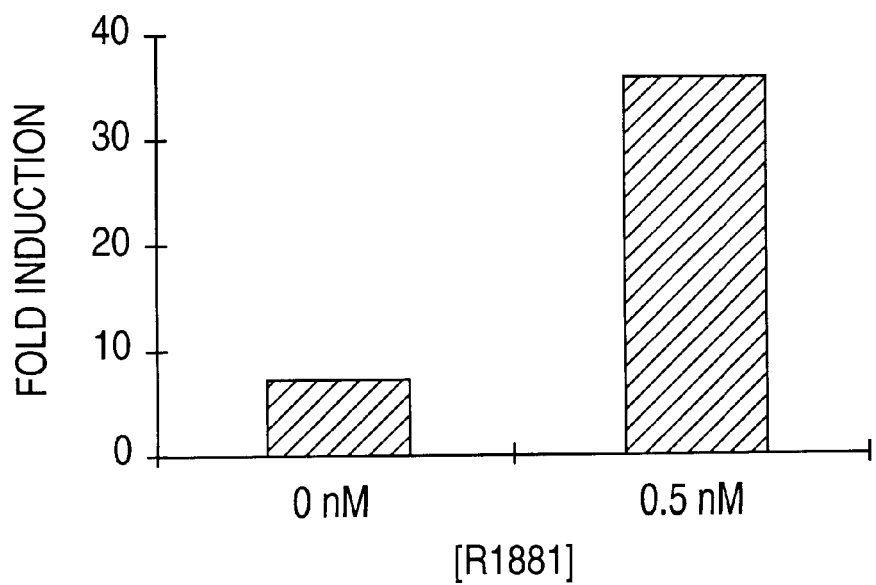

To determine the effect of the 12 kbp 5'-flanking sequence on promoter activity, two constructs were created: CN299 and CN322. The hKLK2 promoter was cloned upstream of the luc gene to create CN299, as described in Example 2. The entire 12 kbp sequence upstream of the hKLK2 gene (including the promoter) was cloned upstream of the luc gene to create CN322, as described in Example 2. Each construct was then used to transfect LNCaP cells. The media in half of the dishes was supplemented with 0.5 nM R1881. The cells were harvested 48 hours post transfection and the luciferase activity was measured. FIGS. 3A and 3B summarize the data and demonstrate that CN322 has higher activity than CN299. At both R1881 concentrations tested, CN322 had higher activity than CN299. At 0 nM, CN322 was 12 fold more active than CN299. At 0.5 nM, CN322 was approximately 36 fold more active than CN299. These data suggest that the 12 kb 5'-flanking sequence contains an enhancer and that this enhancer is also androgen responsive.

Example 4
Characterization of the hKLK2 Enhancer

Figure 4A:
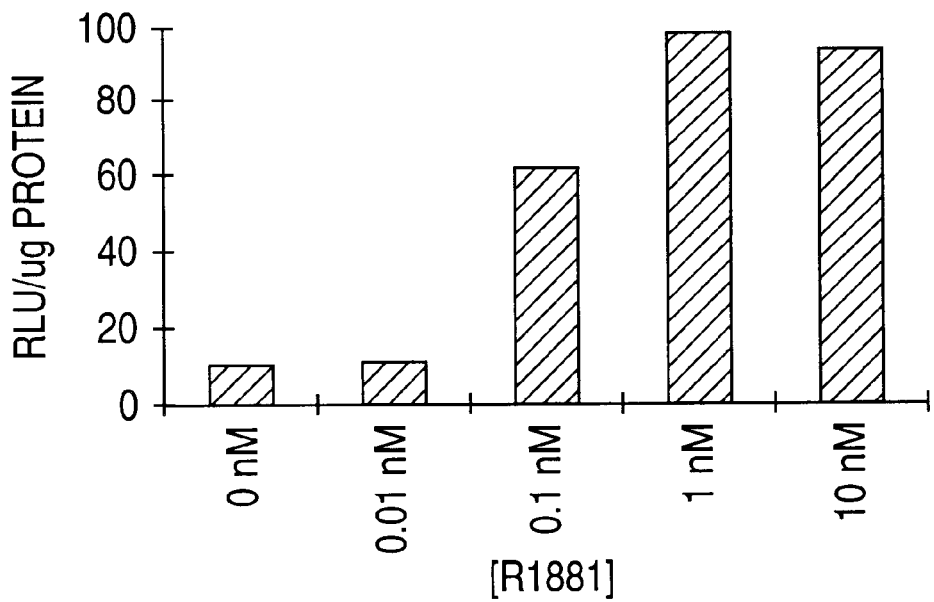
FIGS. 4A and 4B are bar graphs of the concentration dependence of R1881 mediated induction of hKLK2 promoter/enhancer-driven luciferase expression. LNCaP cells were transfected with CN322 and cells were incubated in various concentrations of R1881. Cells were harvested 48 hours after transfection and luciferase activity was measured.
Figure 4B:
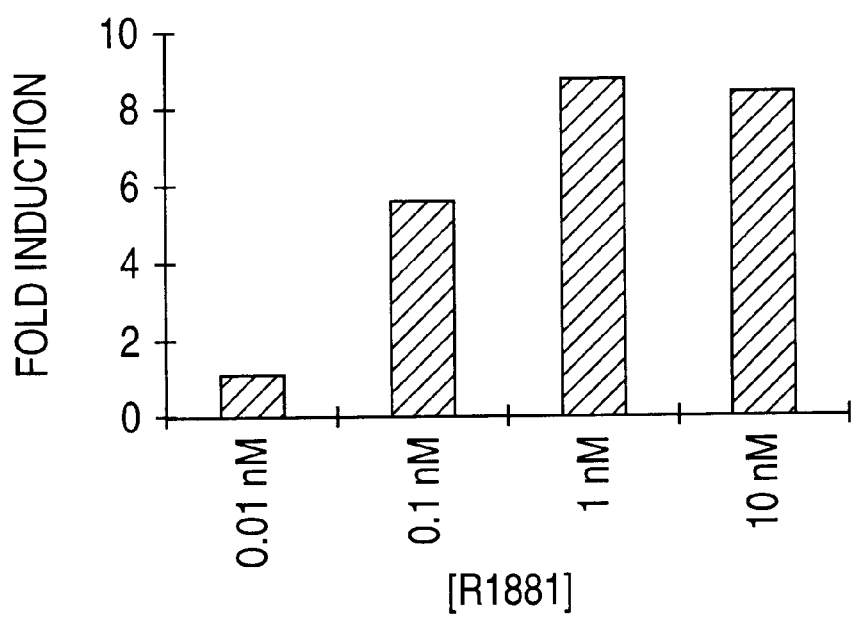

The results of the previous experiment (Example 3) suggested that the luciferase activity of the putative enhancer found in CN322 responded in an androgen dependent manner. To determine if the hKLK2 5'-flanking sequence did indeed contain an androgen responsive element, two experiments were conducted. In the first experiment, LNCaP cells were transfected with CN322, the transformants were incubated in medium containing various concentrations of R1881, and 48 hours after transfection, luciferase activity was measured. The results are summarized in FIGS. 4A and 4B. In short, CN322 responded to the testosterone analog R1881 in a concentration dependent manner. Peak induction of activity was estimated at 1 nM R1881, about 9 fold over the 0 nM activity.

Figure 5:
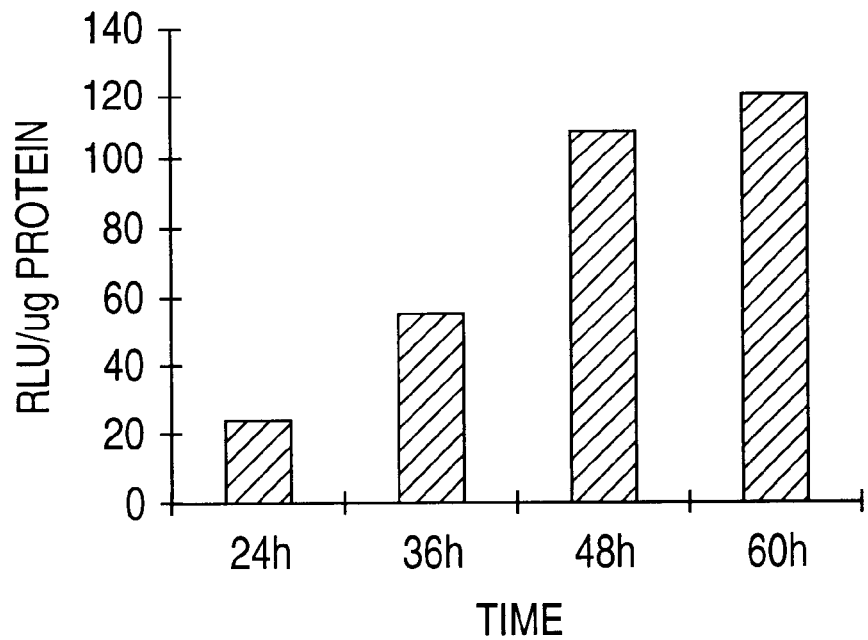
FIG. 5 is a bar graph showing induction of luciferase activity as a function of time of incubation with R1881. LNCaP cells were transfected with CN322 and cells were incubated in medium containing 0.5 nM R1881 for various periods of time, after which luciferase activity was measured.

In the second experiment, the effect of time of incubation in the presence of R1881 on the activity of the 12 kb 5'-flanking sequence was assessed. LNCaP cells were transfected with CN322 and incubated for various periods of time in the presence of 0.5 nM R1881 before harvesting. The results are summarized in FIG. 5. The peak luciferase activity was seen at 60 hours post transfection, but the overall upward trend seemed to plateau at about 48 hours post transfection.

To summarize these two experiments, it seemed that the hKLK2 enhancer appears to be androgen responsive and peak induction of luc activity takes place somewhere between 48 and 60 hours post transfection.

Example 5
Tissue Specificity of the hKLK2 Enhancer

Figure 6:
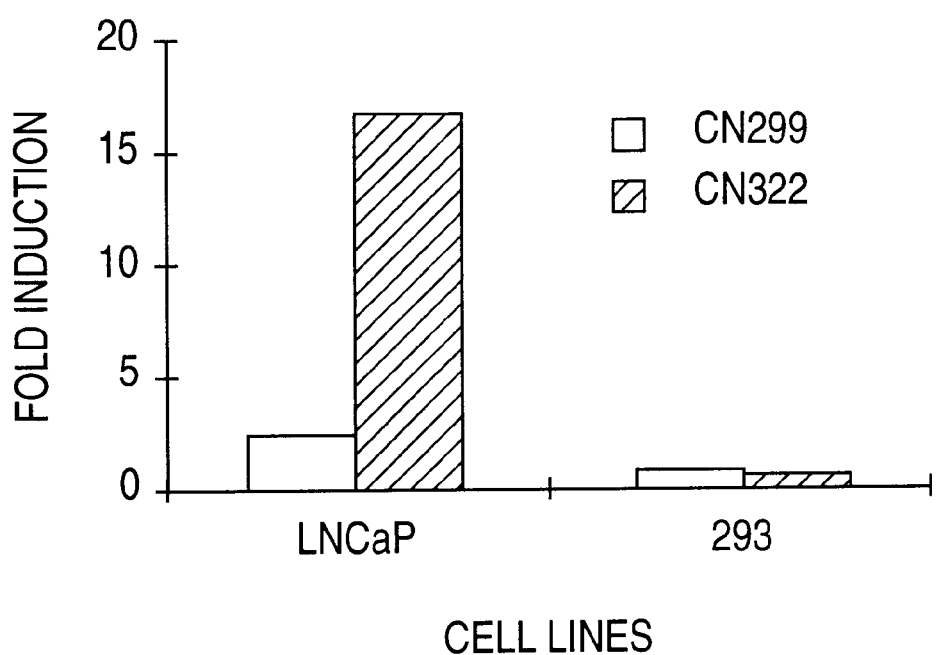
FIG. 6 is a bar graph depicting the cell type specificity of hKLK2 promoter/enhancer-driven luciferase expression. LNCaP or 293 (human embryonal kidney) cells were transfected with CN299 or with CN322 plasmid constructs and incubated in the absence or the presence of 1 nM R1881. Cells were harvested 48 hours post transfection and luciferase activity was measured. Fold induction was calculated by comparing RLU/µg protein with and without 1 nM R1881.

Knowing that the PSA enhancer is tissue specific, a series of experiments was conducted to determine if the same was true for the hKLK2 enhancer. In the first experiment, LNCaP cells (a PSA-producing prostate cancer cell line) and 293s (a human embryonic kidney cell line) were transfected with CN299 or CN322 (Example 2). Half of the dishes were supplemented with 1 nM R1881, and the cells were harvested 48 hours post transfection. The LNCaP cells transfected with CN322 exhibited a 17 fold induction of activity in the presence of 1 nM R1881 when compared to the background activity at 0 nM R1881. The 293s transfected with CN322 showed a reduction of luciferase activity in the presence of 1 nM R1881. CN299 exhibited a 2–3 fold induction in the presence of 1 nM R1881, and a reduction of activity in the 293 cells. The results of this first experiment are summarized in FIG. 6. The results of this experiment again support the conclusion that the hKLK2 enhancer is androgen inducible.

Figure 7:
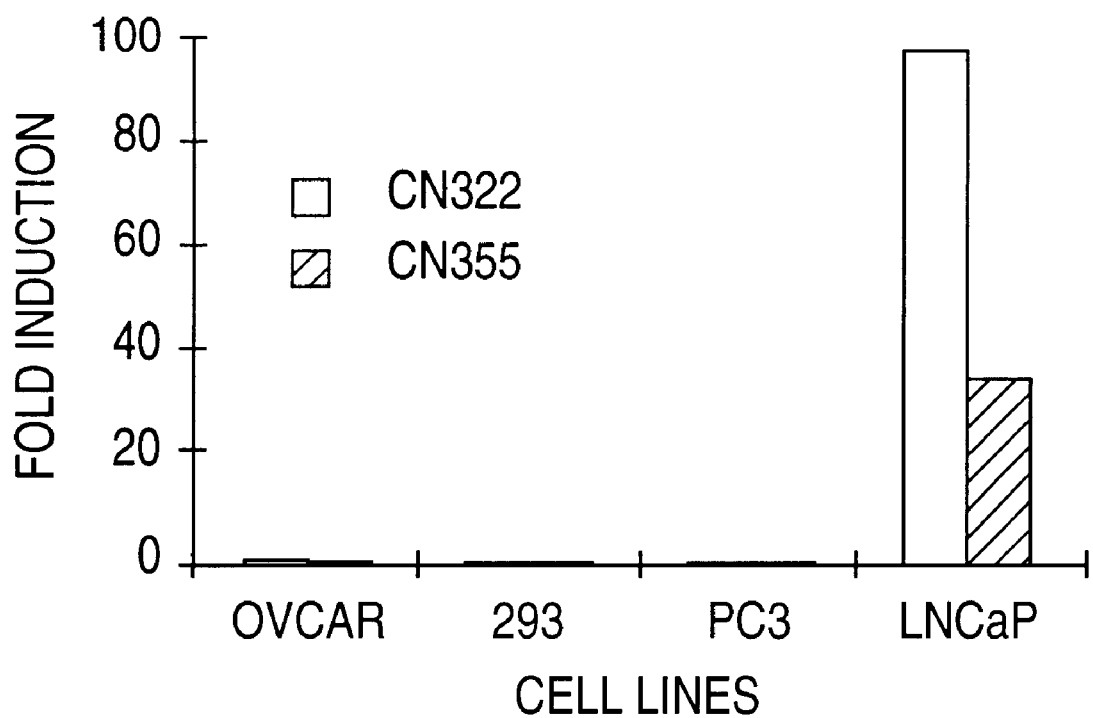
FIG. 7 is a bar graph depicting the activity of the hKLK2 enhancer/promoter in various cell lines. Various cell lines were transfected with either CN322 or CN355, and, after an overnight incubation in complete medium, were incubated in the presence or absence of R1881. CN355 contains a 3.8 kb fragment from approximately −6200 to approximately −2400 of the hKLK2 enhancer fused to the minimal hKLK2 promoter to control luciferase expression. The cell lines used were: OVCAR, human ovarian adenocarcinoma; 293, transformed human primary embryonal kidney; PC3, human grade IV prostate adenocarcinoma; LNCaP, metastatic human prostate adenocarcinoma.

Results of earlier experiments indicated that a putative hKLK2 enhancer may lie between the ApaI site at approximately −6200 bp and the XhoI site at approximately −2400 bp of the hKLK2 enhancer. This 3.8 kbp fragment was fused upstream of the minimal hKLK2 promoter and then cloned upstream of the luc gene, creating CN355. A variety of cell lines were transfected with CN322 or CN355 by incubating them with the complexes in complete media overnight. The complexes were then aspirated and the media was replaced with stripped serum media. The media in half of the plates was supplemented with 1 nM R1881. The cells were then harvested 48 hours after the removal of the DNA-lipid complexes and tested for luciferase activity. The results are summarized in FIG. 7.

CN322 gave almost a 100 fold induction of activity in the presence of 1 nM R1881 in the LNCaP cells. CN355 exhibited a 35-fold induction of activity under the same conditions. All of the other cell lines, including the prostate-derived cell line PC3, showed little androgen inducibility. In fact, CN322 and CN355 showed only about a 1–2 fold induction in any of the other cell lines. Although the PC3 cell line is prostate derived, it lacks an androgen receptor. To further delineate the sequences required for enhancer activity, the construct CN379 was made, which has, in addition to a minimal hKLK2 promoter, the region from −5155 to −3412 driving expression of the luciferase gene. Using the same assay methods described above, this construct gave approximately 54-fold induction of luciferase activity in the presence of inducing agent R1881.

These data show that the minimal enhancer constructs CN355 and CN379 retained some of the activity of the full 12 kbps 5'-flanking sequence, indicating that part of the putative hKLK2 enhancer is between the ApaI and XhoI sites previously described above. The data also support the conclusion that the hKLK2 enhancer is androgen responsive and that its activity is restricted to cell lines containing an androgen receptor.

It is evident from the above results that simple and rapid screening methods are provided for determining activity of compounds in inhibiting proliferation of prostate cancer. The methods employ cells which are stable, can be easily grown, and can be used in a conventional format to identify the activity of specific compounds. The results are at least semi-quantitative, and allow for high throughput screening with automated equipment.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for screening for compounds which alter expression of a prostate-specific enhancer from a human glandular kallikrein (hKLK2) gene, said method employing cells containing an expression construct, said expression construct comprising a transcriptional initiation region of a prostate specific enhancer from a human glandular kallikrein (hKLK2) gene and a promoter and a marker gene whose expression product provides a detectable signal, wherein said marker gene is under the transcriptional control of said transcriptional initiation region, and wherein the cell allows function of the transcriptional initiation region, said method comprising:

(a) combining said cells with a candidate compound and incubating the cells for a sufficient time for detectable expression of said marker gene; and (b) detecting the level of expression of said marker gene as compared to the level of expression in the absence of said candidate compound, wherein an alteration in level of expression in the presence of a candidate compound as compared to expression in the absence of said candidate compound indicates that said candidate compound alters prostate-specific expression.

2. A method according to claim 1, wherein said marker gene expresses an enzyme.

3. A method according to claim 2, wherein said enzyme is luciferase.

4. A method according to claim 3, wherein said detecting comprises:

lysing said cells; and assaying said lysate for luminescence.

5. The method according to claim 1, wherein the hKLK2 enhancer encompasses nucleotides 1 to 9765 of SEQ ID NO: 1 or fragments thereof which regulate transcription of said marker gene.

6. The method according to claim 1, wherein the hKLK2 enhancer encompasses nucleotides 5976 to 9620 of SEQ ID NO: 1 or fragments thereof which regulate transcription of said marker gene.

7. The method according to claim 1, wherein the hKLK2 enhancer encompasses nucleotides 6859–8627 of SEQ ID NO: 1 or fragments thereof which regulate transcription of said marker gene.

8. The method according to claim 1, wherein the cells are prostate cells containing an endogenous androgen receptor.

9. The method according to claim 1, wherein the enhancer is an hKLK2 enhancer and the promoter is an hKLK2 promoter.

10. The method of claim 1, wherein the level of expression in the presence of the compound is reduced, thereby indicating that said compound may be useful for treating prostate cancer.

11. A method according to claim 1, wherein the cells are mammalian.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 12047 base pairs
      (B) TYPE: nucleic acid
      (C) STRANDEDNESS: single
      (D) TOPOLOGY: linear (xi) SEQUENCE DESCRIPTION: SEQ ID NO:1:

```
GAATTCAGAA ATAGGGGAAG GTTGAGGAAG GACACTGAAC TCAAAGGGGA TACAGTGATT     60

GGTTTATTTG TCTTCTCTTC ACAACATTGG TGCTGGAGGA ATTCCCACCC TGAGGTTATG    120

AAGATGTCTG AACACCCAAC ACATAGCACT GGAGATATGA GCTCGACAAG AGTTTCTCAG    180

CCACAGAGAT TCACAGCCTA GGGCAGGAGG ACACTGTACG CCAGGCAGAA TGACATGGGA    240

ATTGCGCTCA CGATTGGCTT GAAGAAGCAA GGACTGTGGG AGGTGGGCTT TGTAGTAACA    300

AGAGGGCAGG GTGAACTCTG ATTCCCATGG GGGAATGTGA TGGTCCTGTT ACAAATTTTT    360

CAAGCTGGCA GGGAATAAAA CCCATTACGG TGAGGACCTG TGGAGGGCGG CTGCCCCAAC    420

TGATAAAGGA AATAGCCAGG TGGGGGCCTT TCCCATTGTA GGGGGGACAT ATCTGGCAAT    480

AGAAGCCTTT GAGACCCTTT AGGGTACAAG TACTGAGGCA GCAAATAAAA TGAAATCTTA    540

TTTTTCAACT TTATACTGCA TGGGTGTGAA GATATATTTG TTTCTGTACA GGGGGTGAGG    600

GAAAGGAGGG GAGGAGGAAA GTTCCTGCAG GTCTGGTTTG GTCTTGTGAT CCAGGGGGTC    660

TTGGAACTAT TTAAATTAAA TTAAATTAAA ACAAGCGACT GTTTTAAATT AAATTAAATT    720

AAATTAAATT TTACTTTATT TTATCTTAAG TTCTGGGCTA CATGTGCAGG ACGTGCAGCT    780

TTGTTACATA GGTAAACGTG TGCCATGGTG GTTTGCTGTA CCTATCAACC CATCACCTAG    840

GTATTAAGCC CAGCATGCAT TAGCTGTTTT TCCTGACGCT CTCCCTCTCC CTGACTCCCA    900

CAACAGGCCC CAGTGTGTGT TGTTCCCCTC CCTGTGTCCA TGTGTTCTCA TTGTTCAGCT    960

CCCACTTATA AGTGAGAACA TGTGGTGTTT GGTTTTCTGT TTCTGTGTTA GTTTGCTGAG   1020

GATAATGGCT TCCACCTCCA TCCATGTTCC TGCAAAGGAC GTGATCTTAT TCTTTTTAT    1080

GGTTGCATAG AAATTGTTTT TACAAATCCA ATTGATATTG TATTTAATTA CAAGTTAATC   1140

TAATTAGCAT ACTAGAAGAG ATTACAGAAG ATATTAGGTA CATTGAATGA GGAAATATAT   1200

AAAATAGGAC GAAGGTGAAA TATTAGGTAG GAAAAGTATA ATAGTTGAAA GAAGTAAAAA   1260

AAAATATGCA TGAGTAGCAG AATGTAAAAG AGGTGAAGAA CGTAATAGTG ACTTTTTAGA   1320

CCAGATTGAA GGACAGAGAC AGAAAAATTT TAAGGAATTG CTAAACCATG TGAGTGTTAG   1380

AAGTACAGTC AATAACATTA AAGCCTCAGG AGGAGAAAAG AATAGGAAAG GAGGAAATAT   1440

GTGAATAAAT AGTAGAGACA TGTTTGATGG ATTTTAAAAT ATTTGAAAGA CCTCACATCA   1500

AAGGATTCAT ACCGTGCCAT TGAAGAGGAA GATGGAAAAG CCAAGAAGCC AGATGAAAGT   1560

TAGAAATATT ATTGGCAAAG CTTAAATGTT AAAAGTCCTA GAGAGAAAGG ATGGCAGAAA   1620

TATTGGCGGG AAAGAATGCA GAACCTAGAA TATAAATTCA TCCCAACAGT TTGGTAGTGT   1680

GCAGCTGTAG CCTTTTCTAG ATAATACACT ATTGTCATAC ATCGCTTAAG CGAGTGTAAA   1740

ATGGTCTCCT CACTTTATTT ATTTATATAT TTATTTAGTT TTGAGATGGA GCCTCGCTCT   1800
```

```
GTCTCCTAGG CTGGAGTGCA ATAGTGCGAT ACCACTCACT GCAACCTCTG CCTCCTCTGT    1860

TCAAGTGATT TTCTTACCTC AGCCTCCCGA GTAGCTGGGA TTACAGGTGC GTGCCACCAC    1920

ACCCGGCTAA TTTTTGTATT TTTTGTAGAG ACGGGGTTTT GCCATGTTGG CCAGGCTGGT    1980

CTTGAACTCC TGACATCAGG TGATCCACCT GCCTTGGCCT CCTAAAGTGC TGGGATTACA    2040

GGCATGAGCC ACCGTGCCCA ACCACTTTAT TTATTTTTTA TTTTTATTTT TAAATTTCAG    2100

CTTCTATTTG AAATACAGGG GGCACATATA TAGGATTGTT ACATGGGTAT ATTGAACTCA    2160

GGTAGTGATC ATACTACCCA ACAGGTAGGT TTTCAACCCA CTCCCCCTCT TTTCCTCCCC    2220

ATTCTAGTAG TGTGCAGTGT CTATTGTTCT CATGTTTATG TCTATGTGTG CTCCAGGTTT    2280

AGCTCCCACC TGTAAGTGAG AACGTGTGG ATTTGATTTT CTGTCCCTGT GTTAATTCAC    2340

TTAGGATTAT GGCTTCCAGC TCCATTCATA TTGCTGTAAA GGATATGATT CATTTTTCAT    2400

GGCCATGCAG TATTCCATAT TGCGTATAGA TCACATTTTC TTTCTTTTTT TTTTTGAGA    2460

CGGAGTCTTG CTTTGCTGCC TAGGCTGGAG TGCAGTAGCA CGATCTCGGC TCACTGCAAG    2520

CTTCACCTCC GGGGTTCACG TCATTCTTCT GTCTCAGCTT CCCAAGTAGC TGGGACTACA    2580

GGCGCCCGCC ACCACGTCCG GCTAATTTTT TTGTGTGTTT TTAGTAGAGA TGGGGGTTTC    2640

ACTGTGTTAG CCAGGATGGT CTTGATCTCC TGACCTTGTG GTCCACCTGC CTCGGTCTCC    2700

CAAAGTGCTG GGATTACAGG GGTGAGCCAC TGCGCCCGGC CCATATATAC CACATTTTCT    2760

TTAACCAATC CACCATTGAT GGGCAACTAG GTAGATTCCA TGGATTCCAC AGTTTTGCTA    2820

TTGTGTGCAG TGTGGCAGTA GACATATGAA TGAATGTGTC TTTTTGGTAT AATGATTTGC    2880

ATTCCTTTGG GTATACAGTC ATTAATAGGA GTGCTGGGTT GAACGGTGGC TCTGTTTAAA    2940

ATTCTTTGAG AATTTTCCAA ACTGTTTGCC ATAGAGAGCA AACTAATTTA CATTTCCACG    3000

AACAGTATAT AAGCATTCCC TTTTCTCCAC AGCTTTGTCA TCATGGTTTT TTTTTTTCTT    3060

TATTTTAAAA AAGAATATGT TGTTGTTTTC CCAGGGTACA TGTGCAGGAT GTGCAGGTTT    3120

GTTACATAGG TAGTAAACGT GAGCCATGGT GGTTTGCTGC ACCTGTCAAC CCATTACCTG    3180

GGTATGAAGC CCTGCCTGCA TTAGCTCTTT TCCCTAATGC TCTCACTACT GCCCCACCCT    3240

CACCCTGACA GGGCAAACAG ACAACCTACA GAATGGGAGG AAATTTTTGC AATCTATTCA    3300

TCTGACAAAG GTCAAGAATA TCCAGAATCT ACAAGGAACT TAAGCAAATT TTTACTTTTT    3360

AATAATAGCC ACTCTGACTG GCGTGAAATG GTATCTCATT GTGGTTTTCA TTTGAATTTC    3420

TCTGATGATC AGTGACGATG AGCATTTTTT CATATTTGTT GGCTGCTTGT ACGTCTTTTG    3480

AGAAGTGTCT CTTCATGCCT TTTGGCCACT TTAATGGGAT TATTTTTTGC TTTTTAGTTT    3540

AAGTTCCTTA TAGATTCTGG ATATTAGACT TCTTATTGGA TGCATAGTTT GTGAATACTC    3600

TCTTCCATTC TGTAGGTTGT CTGTTTACTC TATTGATGGC TTCTTTTGCT GTGCCGAAGC    3660

ATCTTAGTTT AATTAGAAAC CACCTGCCAA TTTTTGTTTT TGTTGCAATT GCTTTTGGGG    3720

ACTTAGTCAT AAACTCTTTG CCAAGGTCTG GGTCAAGAAG AGTATTTCCT AGGTTTTCTT    3780

CTAGAATTTT GAAAGTCTGA ATGTAAACAT TTGCATTTTT AATGCATCTT GAGTTAGTTT    3840

TTGTATATGT GAAAGGTCTA CTCTCATTTT CTTTCCCTCT TTCTTTCTTT CTTTCTTTTC    3900

TTTCTTTCTT TCTTTCTTTC TTTCTTTCTT TCTTTCTTTC TTTCTTTTTG TCCTTCTTTC    3960

TTTCTTTCTT TCTCTTTCTT TCTCTCTTTC TTTTTTTTTT TTGATGGAGT ATTGCTCTGT    4020

TGCCCAGGCT GCAGTGCAGC GGCACGATCT CGGCTCACTG CAACCTCTGC CTCCTGGGTT    4080

CAACTGATTC TCCTGCATCA GCCTTCCAAG TAGCTGGGAT TATAGGCGCC CGCCACCACG    4140
```

```
CCCGACTAAT TTTTGTATTT TTAGTAGAGA CGGGGTTGTG CCATGTTGGC CAGGCTGGTT    4200

TGAAACTCCT GACCTCAAAC GATCTGCCTG CCTTGGCCTC CCAAAGTGCT GGGATTACAG    4260

GTGTGAGCCA CTGTGCCCAG CCAAGAATGT CATTTTCTAA GAGGTCCAAG AACCTCAAGA    4320

TATTTTGGGA CCTTGAGAAG AGAGGAATTC ATACAGGTAT TACAAGCACA GCCTAATGGC    4380

AAATCTTTGG CATGGCTTGG CTTCAAGACT TTAGGCTCTT AAAAGTCGAA TCCAAAAATT    4440

TTTATAAAAG CTCCAGCTAA GCTACCTTAA AAGGGGCCTG TATGGCTGAT CACTCTTCTT    4500

GCTATACTTT ACACAAATAA ACAGGCCAAA TATAATGAGG CCAAAATTTA TTTTGCAAAT    4560

AAATTGGTCC TGCTATGATT TACTCTTGGT AAGAACAGGG AAAATAGAGA AAAATTTAGA    4620

TTGCATCTGA CCTTTTTTTC TGAATTTTTA TATGTGCCTA CAATTTGAGC TAAATCCTGA    4680

ATTATTTTCT GGTTGCAAAA ACTCTCTAAA GAAGAACTTG GTTTTCATTG TCTTCGTGAC    4740

ACATTTATCT GGCTCTTTAC TAGAACAGCT TTCTTGTTTT TGGTGTTCTA GCTTGTGTGC    4800

CTTACAGTTC TACTCTTCAA ATTATTGTTA TGTGTATCTC ATAGTTTTCC TTCTTTTGAG    4860

AAAACTGAAG CCATGGTATT CTGAGGACTA GAGATGACTC AACAGAGCTG GTGAATCTCC    4920

TCATATGCAA TCCACTGGGC TCGATCTGCT TCAAATTGCT GATGCACTGC TGCTAAAGCT    4980

ATACATTTAA AACCCTCACT AAAGGATCAG GGACCATCAT GGAAGAGGAG GAAACATGAA    5040

ATTGTAAGAG CCAGATTCGG GGGGTAGAGT GTGGAGGTCA GAGCAACTCC ACCTTGAATA    5100

AGAAGGTAAA GCAACCTATC CTGAAAGCTA ACCTGCCATG GTGGCTTCTG ATTAACCTCT    5160

GTTCTAGGAA GACTGACAGT TTGGGTCTGT GTCATTGCCC AAATCTCATG TTAAATTGTA    5220

ATCCCCAGTG TTCGGAGGTG GGACTTGGTG GTAGGTGATT CGGTCATGGG AGTAGATTTT    5280

CTTCTTTGTG GTGTTACAGT GATAGTGAGT GAGTTCTCGT GAGATCTGGT CATTTAAAAG    5340

TGTGTGGCCC CTCCCCTCCC TCTCTTGGTC CTCCTACTGC CATGTAAGAT ACCTGCTCCT    5400

GCTTTGCCTT CTACCATAAG TAAAAGCCCC CTGAGGCCTC CCCAGAAGCA GATGCCACCA    5460

TGCTTCCTGT ACAGCCTGCA GAACCATCAG CCAATTAAAC CTCTTTTCTG TATAAATTAC    5520

CAGTCTTGAG TATCTCTTTA CAGCAGTGTG AGAACGGACT AATACAAGGG TCTCCAAAAT    5580

TCCAAGTTTA TGTATTCTTT CTTGCCAAAT AGCAGGTATT TACCATAAAT CCTGTCCTTA    5640

GGTCAAACAA CCTTGATGGC ATCGTACTTC AATTGTCTTA CACATTCCTT CTGAATGACT    5700

CCTCCCCTAT GGCATATAAG CCCTGGGTCT TGGGGATAAA TGGCAGAGGG GTCCACCATC    5760

TTGTCTGGCT GCCACCTGAG ACACGGACAT GGCTTCTGTT GGTAAGTCTC TATTAAATGT    5820

TTCTTTCTAA GAAACTGGAT TTGTCAGCTT GTTTCTTTGG CCTCTCAGCT TCCTCAGACT    5880

TTGGGGTAGG TTGCACAACC CTGCCCACCA CGAAACAAAT GTTTAATATG ATAAATATGG    5940

ATAGATATAA TCCACATAAA TAAAAGCTCT TGGAGGGCCC TCAATAATTG TTAAGAGTGT    6000

AAATGTGTCC AAAGATGGAA AATGTTTGAG AACTACTGTC CCAGAGATTT TCCTGAGTTC    6060

TAGAGTGTGG GAATATAGAA CCTGGAGCTT GGCTTCTTCA GCCTAGAATC AGGAGTATGG    6120

GGCTGAAGTC TGAAGCTTGG CTTCAGCAGT TTGGGGTTGG CTTCCGGAGC ACATATTTGA    6180

CATGTTGCGA CTGTGATTTG GGGTTTGGTA TTTGCTCTGA ATCCTAATGT CTGTCCTTGA    6240

GGCATCTAGA ATCTGAAATC TGTGGTCAGA ATTCTATTAT CTTGAGTAGG ACATCTCCAG    6300

TCCTGGTTCT GCCTTCTAGG GCTGGAGTCT GTAGTCAGTG ACCCGGTCTG GCATTTCAAC    6360

TTCATATACA GTGGGCTATC TTTTGGTCCA TGTTTCAACC AAACAACCGA ATAAACCATT    6420

AGAACCTTTC CCCACTTCCC TAGCTGCAAT GTTAAACCTA GGATTTCTGT TTAATAGGTT    6480
```

```
CATATGAATA ATTTCAGCCT GATCCAACTT TACATTCCTT CTACCGTTAT TCTACACCCA    6540

CCTTAAAAAT GCATTCCCAA TATATTCCCT GGATTCTACC TATATATGGT AATCCTGGCT    6600

TTGCCAGTTT CTAGTGCATT AACATACCTG ATTTACATTC TTTTACTTTA AAGTGGAAAT    6660

AAGAGTCCCT CTGCAGAGTT CAGGAGTTCT CAAGATGGCC CTTACTTCTG ACATCAATTG    6720

AGATTTCAAG GGAGTCGCCA AGATCATCCT CAGGTTCAGT GATTGCTGGT AGCCCTCATA    6780

TAACTCAATG AAAGCTGTTA TGCTCATGGC TATGGTTTAT TACAGCAAAA GAATAGAGAT    6840

GAAAATCTAG CAAGGGAAGA GTTGCATGGG GCAAAGACAA GGAGAGCTCC AAGTGCAGAG    6900

ATTCCTGTTG TTTTCTCCCA GTGGTGTCAT GGAAAGCAGT ATCTTCTCCA TACAATGATG    6960

TGTGATAATA TTCAGTGTAT TGCCAATCAG GGAACTCAAC TGAGCCTTGA TTATATTGGA    7020

GCTTGGTTGC ACAGACATGT CGACCACCTT CATGGCTGAA CTTTAGTACT TAGCCCCTCC    7080

AGACGTCTAC AGCTGATAGG CTGTAACCCA ACATTGTCAC CATAAATCAC ATTGTTAGAC    7140

TATCCAGTGT GGCCCAAGCT CCCGTGTAAA CACAGGCACT CTAAACAGGC AGGATATTTC    7200

AAAAGCTTAG AGATGACCTC CCAGGAGCTG AATGCAAAGA CCTGGCCTCT TTGGGCAAGG    7260

AGAATCCTTT ACCGCACACT CTCCTTCACA GGGTTATTGT GAGGATCAAA TGTGGTCATG    7320

TGTGTGAGAC ACCAGCACAT GTCTGGCTGT GGAGAGTGAC TTCTATGTGT GCTAACATTG    7380

CTGAGTGCTA AGAAAGTATT AGGCATGGCT TTCAGCACTC ACAGATGCTC ATCTAATCCT    7440

CACAACATGG CTACAGGGTG GGCACTACTA GCCTCATTTG ACAGAGGAAA GGACTGTGGA    7500

TAAGAAGGGG GTGACCAATA GGTCAGAGTC ATTCTGGATG CAAGGGGCTC CAGAGGACCA    7560

TGATTAGACA TTGTCTGCAG AGAAATTATG GCTGGATGTC TCTGCCCCGG AAAGGGGGAT    7620

GCACTTTCCT TGACCCCCTA TCTCAGATCT TGACTTTGAG GTTATCTCAG ACTTCCTCTA    7680

TGATACCAGG AGCCCATCAT AATCTCTCTG TGTCCTCTCC CCTTCCTCAG TCTTACTGCC    7740

CACTCTTCCC AGCTCCATCT CCAGCTGGCC AGGTGTAGCC ACAGTACCTA ACTCTTTGCA    7800

GAGAACTATA AATGTGTATC CTACAGGGGA GAAAAAAAA AAGAACTCTG AAAGAGCTGA    7860

CATTTTACCG ACTTGCAAAC ACATAAGCTA ACCTGCCAGT TTTGTGCTGG TAGAACTCAT    7920

GAGACTCCTG GGTCAGAGGC AAAAGATTTT ATTACCCACA GCTAAGGAGG CAGCATGAAC    7980

TTTGTGTTCA CATTTGTTCA CTTTGCCCCC CAATTCATAT GGATGATCA GAGCAGTTCA    8040

GGTGGATGGA CACAGGGGTT TGTGGCAAAG GTGAGCAACC TAGGCTTAGA AATCCTCAAT    8100

CTTATAAGAA GGTACTAGCA AACTTGTCCA GTCTTTGTAT CTGACGGAGA TATTATCTTT    8160

ATAATTGGGT TGAAAGCAGA CCTACTCTGG AGGAACATAT TGTATTTATT GTCCTGAACA    8220

GTAAACAAAT CTGCTGTAAA ATAGACGTTA ACTTTATTAT CTAAGGCAGT AAGCAAACCT    8280

AGATCTGAAG GCGATACCAT CTTGCAAGGC TATCTGCTGT ACAAATATGC TTGAAAAGAT    8340

GGTCCAGAAA AGAAAACGGT ATTATTGCCT TTGCTCAGAA GACACACAGA AACATAAGAG    8400

AACCATGGAA AATTGTCTCC CAACACTGTT CACCCAGAGC CTTCCACTCT TGTCTGCAGG    8460

ACAGTCTTAA CATCCCATCA TTAGTGTGTC TACCACATCT GGCTTCACCG TGCCTAACCA    8520

AGATTTCTAG GTCCAGTTCC CCACCATGTT TGGCAGTGCC CCACTGCCAA CCCCAGAATA    8580

AGGGAGTGCT CAGAATTCCG AGGGGACATG GGTGGGGATC AGAACTTCTG GGCTTGAGTG    8640

CAGAGGGGC CCATACTCCT TGGTTCCGAA GGAGGAAGAG GCTGGAGGTG AATGTCCTTG    8700

GAGGGAGGA ATGTGGGTTC TGAACTCTTA AATCCCCAAG GGAGGAGACT GGTAAGGTCC    8760

CAGCTTCCGA GGTACTGACG TGGGAATGGC CTGAGAGGTC TAAGAATCCC GTATCCTCGG    8820
```

```
GAAGGAGGGG CTGAAATTGT GAGGGGTTGA GTTGCAGGGG TTTGTTAGCT TGAGACTCCT   8880
TGGTGGGTCC CTGGGAAGCA AGGACTGGAA CCATTGGCTC CAGGGTTTGG TGTGAAGGTA   8940
ATGGGATCTC CTGATTCTCA AAGGGTCAGA GGACTGAGAG TTGCCCATGC TTTGATCTTT   9000
CCATCTACTC CTTACTCCAC TTGAGGGTAA TCACCTACTC TTCTAGTTCC ACAAGAGTGC   9060
GCCTGCGCGA GTATAATCTG CACATGTGCC ATGTCCCGAG GCCTGGGGCA TCATCCACTC   9120
ATCATTCAGC ATCTGCGCTA TGCGGGCGAG GCCGGCGCCA TGACGTCATG TAGCTGCGAC   9180
TATCCCTGCA GCGCGCCTCT CCCGTCACGT CCCAACCATG GAGCTGTGGA CGTGCGTCCC   9240
CTGGTGGATG TGGCCTGCGT GGTGCCAGGC CGGGGCCTGG TGTCCGATAA AGATCCTAGA   9300
ACCACAGGAA ACCAGGACTG AAAGGTGCTA GAGAATGGCC ATATGTCGCT GTCCATGAAA   9360
TCTCAAGGAC TTCTGGGTGG AGGGCACAGG AGCCTGAACT TACGGGTTTG CCCCAGTCCA   9420
CTGTCCTCCC AAGTGAGTCT CCCAGATACG AGGCACTGTG CCAGCATCAG CTTCATCTGT   9480
ACCACATCTT GTAACAGGGA CTACCCAGGA CCCTGATGAA CACCATGGTG TGTGCAGGAA   9540
GAGGGGGTGA AGGCATGGAC TCCTGTGTGG TCAGAGCCCA GAGGGGCCA TGACGGGTGG    9600
GGAGGAGGCT GTGGACTGGC TCGAGAAGTG GGATGTGGTT GTGTTTGATT TCCTTTGGCC   9660
AGATAAAGTG CTGGATATAG CATTGAAAAC GGAGTATGAA GACCAGTTAG AATGGAGGGT   9720
CAGGTTGGAG TTGAGTTACA GATGGGGTAA AATTCTGCTT CGGATGAGTT TGGGGATTGG   9780
CAATCTAAAG GTGGTTTGGG ATGGCATGGC TTTGGGATGG AAATAGGTTT GTTTTTATGT   9840
TGGCTGGGAA GGGTGTGGGG ATTGAATTGG GGATGAAGTA GGTTTAGTTT TGGAGATAGA   9900
ATACATGGAG CTGGCTATTG CATGCGAGGA TGTGCATTAG TTTGGTTTGA TCTTTAAATA   9960
AAGGAGGCTA TTAGGGTTGT CTTGAATTAG ATTAAGTTGT GTTGGGTTGA TGGGTTGGGC  10020
TTGTGGGTGA TGTGGTTGGA TTGGGCTGTG TTAAATTGGT TTGGGTCAGG TTTTGGTTGA  10080
GGTTATCATG GGGATGAGGA TATGCTTGGG ACATGGATTC AGGTGGTTCT CATTCAAGCT  10140
GAGGCAAATT TCCTTTCAGA CGGTCATTCC AGGGAACGAG TGGTTGTGTG GGGGAAATCA  10200
GGCCACTGGC TGTGAATATC CCTCTATCCT GGTCTTGAAT TGTGATTATC TATGTCCATT  10260
CTGTCTCCTT CACTGTACTT GGAATTGATC TGGTCATTCA GCTGGAAATG GGGGAAGATT  10320
TTGTCAAATT CTTGAGACAC AGCTGGGTCT GGATCAGCGT AAGCCTTCCT TCTGGTTTTA  10380
TTGAACAGAT GAAATCACAT TTTTTTTTTC AAAATCACAG AAATCTTATA GAGTTAACAG  10440
TGGACTCTTA TAATAAGAGT TAACACCAGG ACTCTTATTC TTGATTCTTT TCTGAGACAC  10500
CAAAATGAGA TTTCTCAATG CCACCCTAAT TCTTTTTTTT TTTTTTTTT TTTTTGAGAC   10560
ACAGTCTGGG TCTTTTGCTC TGTCACTCAG GCTGGAGCGC AGTGGTGTGA TCATAGCTCA  10620
CTGAACCCTT GACCTCCTGG ACTTAAGGGA TCCTCCTGCT TCAGCCTCCT GAGTAGATGG  10680
GGCTACAGGT GCTTGCCACC ACACCTGGCT AATTAAATTT TTTTTTTTTT TTTGTAGAGA  10740
AAGGGTCTCA CTTTGTTGCC CTGGCTGATC TTGAACTTCT GACTTCAAGT GATTCTTCAG  10800
CCTTGGACTC CCAAAGCACT GGGATTGCTG GCATGAGCCA CTCACCGTGC CTGGCTTGCA  10860
GCTTAATCTT GGAGTGTATA AACCTGGCTC CTGATAGCTA GACATTTCAG TGAGAAGGAG  10920
GCATTGGATT TTGCATGAGG ACAATTCTGA CCTAGGAGGG CAGGTCAACA GGAATCCCCG  10980
CTGTACCTGT ACGTTGTACA GGCATGGAGA ATGAGGAGTG AGGAGGCCGT ACCGGAACCC  11040
CATATTGTTT AGTGGACATT GGATTTTGAA ATAATAGGGA ACTTGGTCTG GGAGAGTCAT  11100
ATTTCTGGAT TGGACAATAT GTGGTATCAC AAGGTTTTAT GATGAGGGAG AAATGTATGT  11160
```

```
                                                              -continued

GGGGAACCAT TTTCTGAGTG TGGAAGTGCA AGAATCAGAG AGTAGCTGAA TGCCAACGCT     11220

TCTATTTCAG GAACATGGTA AGTTGGAGGT CCAGCTCTCG GGCTCAGACG GGTATAGGGA     11280

CCAGGAAGTC TCACAATCCG ATCATTCTGA TATTTCAGGG CATATTAGGT TTGGGGTGCA     11340

AAGGAAGTAC TTGGGACTTA GGCACATGAG ACTTTGTATT GAAAATCAAT GATTGGGGCT     11400

GGCCGTGGTG CTCACGCCTG TAATCTCATC ACTTTGGGAG ACCGAAGTGG GAGGATGGCT     11460

TGATCTCAAG AGTTGGACAC CAGCCTAGGC AACATGGCCA GACCCTCTCT CTACAAAAAA     11520

ATTAAAAATT AGCTGGATGT GGTGGTGCAT GCTTGTGGTC TCAGCTATCC TGGAGGCTGA     11580

GACAGGAGAA TCGGTTGAGT CTGGGAGTTC AAGGCTACAG GGAGCTGCGA TCACGCCGCT     11640

GCACTCCAGC CTGGGAAACA GAGTGAGACT GTCTCAGAAT TTTTTTAAAA AAGAATCAGT     11700

GATCATCCCA ACCCCTGTTG CTGTTCATCC TGAGCCTGCC TTCTCTGGCT TTGTTCCCTA     11760

GATCACATCT CCATGATCCA TAGGCCCTGC CCAATCTGAC CTCACACCGT GGGAATGCCT     11820

CCAGACTGAT CTAGTATGTG TGGAACAGCA AGTGCTGGCT CTCCCTCCCC TTCCACAGCT     11880

CTGGGTGTGG GAGGGGGTTG TCCAGCCTCC AGCAGCATGG GGAGGGCCTT GGTCAGCATC     11940

TAGGTGCCAA CAGGGCAAGG GCGGGGTCCT GGAGAATGAA GGCTTTATAG GGCTCCTCAG     12000

GGAGGCCCCC CAGCCCCAAA CTGCACCACC TGGCCGTGGA CACCGGT                   12047

(2) INFORMATION FOR SEQ ID NO:2:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (xi) SEQUENCE DESCRIPTION: SEQ ID NO:2:

GATCACCGGT GCTCACGCCT GTAATCTCAT CAC                                     33
```